United States Patent [19]

Gimpelson

[11] Patent Number: 5,336,239
[45] Date of Patent: Aug. 9, 1994

[54] SURGICAL NEEDLE

[76] Inventor: Richard J. Gimpelson, 1028 Terrace Rock Cir., Ballwin, Mo. 63011

[21] Appl. No.: 4,925
[22] Filed: Jan. 15, 1993
[51] Int. Cl.⁵ .............................................. A61B 17/06
[52] U.S. Cl. .................................................... 606/223
[58] Field of Search .................. 606/223, 222, 148; 604/264, 272, 273, 274; 112/222; 223/102

[56] References Cited

U.S. PATENT DOCUMENTS

| | | | |
|---|---|---|---|
| 377,160 | 1/1888 | Hunter | 223/102 |
| 818,152 | 4/1906 | Edwards | 606/225 |
| 1,110,468 | 9/1914 | Turner | 606/223 |
| 1,377,359 | 5/1921 | Littlejohn . | |
| 3,116,707 | 1/1964 | Newman | 112/222 |
| 3,160,157 | 12/1964 | Chisman | 606/224 |
| 4,527,564 | 7/1985 | Eguchi et al. | 606/223 |
| 4,586,926 | 5/1986 | Osborne | 604/272 |
| 5,059,207 | 10/1991 | Shah | 223/102 |
| 5,112,344 | 5/1992 | Petros | 606/148 |

FOREIGN PATENT DOCUMENTS 309633 4/1929 United Kingdom ................ 606/222

Primary Examiner—Tamara L. Graysay
Attorney, Agent, or Firm—Grace J. Fishel

[57] ABSTRACT

A surgical needle for use in narrow, deep incisions in the abdominal wall opening into the abdominal cavity. The needle can be used to suture laparoscopic incisions and to suture an artery, ligament and the like which is reached through the incision. The needle has an elongated shaft with a proximally directed hook at its distal end. At its proximal end, there is a handle or indicia for indicating the direction of the hook. The hook is pointed and has an eye adjacent its point through which a suture can be threaded. The hook is of a size and shape that it can be inserted through the incision and manipulated from the opening of the shaft to place the suture "through and through" a selected portion of the abdominal wall from the base of the incision.

15 Claims, 4 Drawing Sheets

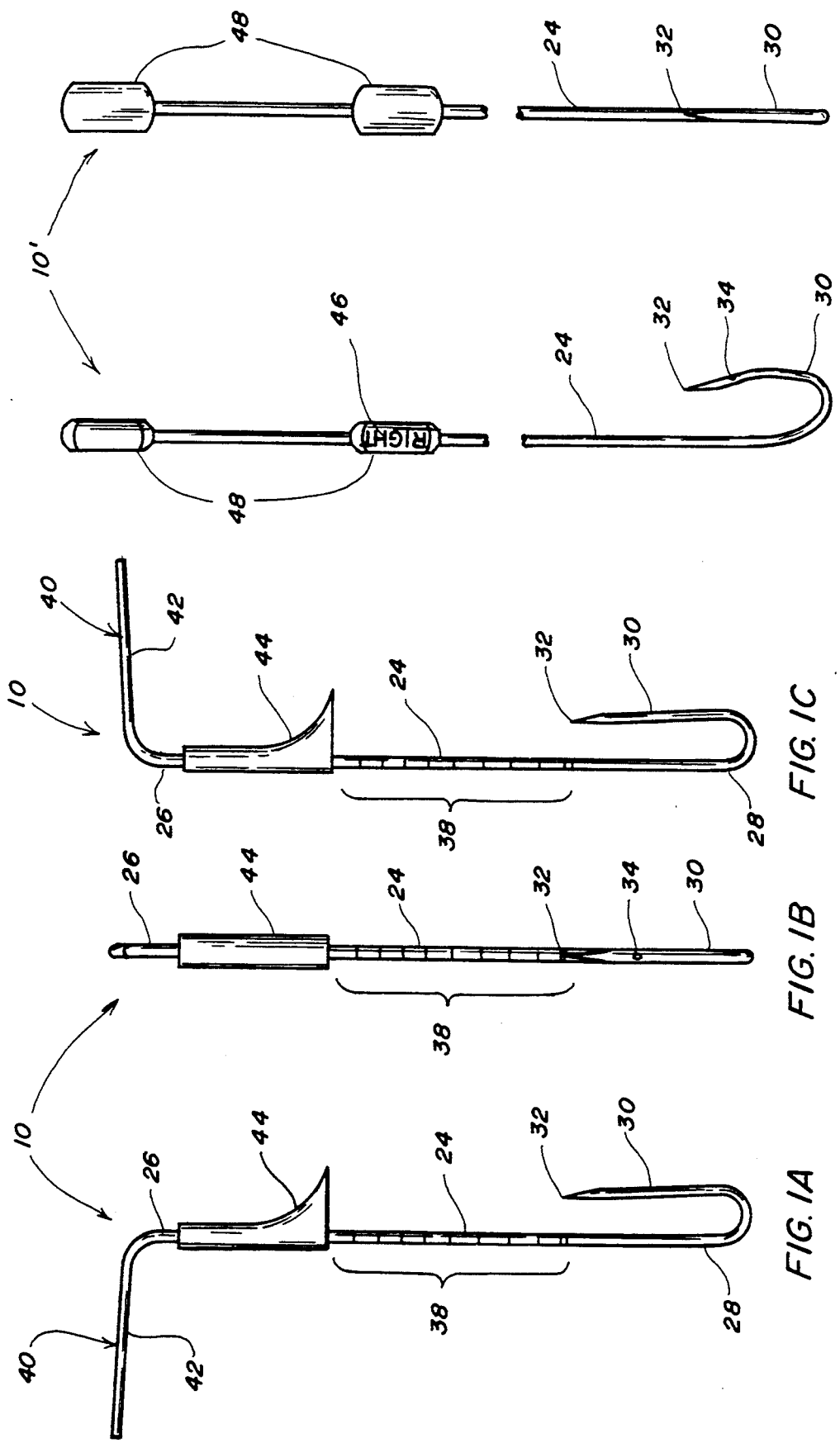

SURGICAL NEEDLE

BACKGROUND OF THE INVENTION

1. Field of the Invention

The present invention relates to a surgical needle for closing laparoscopic incisions to prevent the development of hernias. The device may also be used for suturing an artery, ligament and the like which is reached through a laparoscopic incision and for other surgical procedures which require suturing of deep but narrow wounds.

2. Brief Description of the Prior Art

Surgical procedures such as laparoscopy have created a need for a surgical needle capable of closing a small, deep incision through multiple layers of tissues. At first, laparoscopic incisions tended to be small and did not require closure. Larger incisions are now common to accommodate larger instruments and removal of tissue specimens. As reported by Kadar N., Reich H., Liu C. Y., Manko G. F. and Gimpelson R. J. in an article entitled "Incisional hernias following major laparoscopic gynecological procedures" accepted for publication in the American Journal of Obstetrics and Gynecology, the incidence of incisional hernia is greatly increased when a 10 mm or larger trocar is used at an extra-umbilical site. When the incision is 10 mm or larger, the authors believe that the underlying fascia should be closed and that even the peritoneum may require closure at a 12 mm and larger site.

There are straight needles for closing a laparoscopic incision that have a suture attached to the end of the needle opposite the point and straight needles with a suture attached adjacent the point. Both types of straight needles must be worked inside the patient and require the use of graspers. For example, when a suture is attached opposite the point, the needle is inserted down into the abdominal wall on one side of an incision and then with much difficulty manipulated with laparoscopic graspers at the base of the incision and inserted up through the abdominal wall on the other side of the incision.

Straight needles with an eye adjacent the end are inserted through the abdominal wall on one side of the incision. The suture is then unthreaded from the needle and rethreaded into the eye of the needle inserted on the other side of the incision. Laparoscopic graspers in the abdominal cavity are used for this difficult and time consuming procedure.

Curved needles are also used for closing a laparoscopic incision. They can be worked outside the patient but they require the use of a needle holder. The suture is usually attached to the end of the curved needle opposite the point and it is nearly impossible to determine just where the point is going. Great damage can result from accidentally penetrating tissues.

SUMMARY OF THE INVENTION

In view of the above, it is an object of the present invention to provide a curved surgical needle for closing laparoscopic incisions that allows a surgeon to accurately locate the point. It is another object to provide a needle that can be worked without a needle holder or laparoscopic grasper from the outside to place a "through and through" suture in the abdominal wall. It is also an object to provide a needle which can be used to suture an artery or ligament reached from a narrow incision where suturing is otherwise difficult. Other objects and features of the invention will be in part apparent and in part pointed out hereinafter.

In accordance with the invention, a surgical needle is provided with an elongated shaft having a proximal end and a distal end. The shaft has a hook at its distal end that is adapted in size and shape to be passed through a narrow incision in an abdominal wall. The hook terminates in a point with an eye adjacent the point for receipt of a suture. The hook is of a length that when it is inserted in a selected portion of the abdominal wall surrounding the incision starting at the base of the incision, the point sticks through the wall sufficiently far to expose the eye from the opening of the incision. The shaft has a means at its proximal end for indicating the location of the point so that working from the outside the needle can be manipulated at the base of the incision to accurately place the suture through and through the abdominal wall. Still working from the outside, a knot can then be tied in the suture bringing together that part of the abdominal wall between the "through and through" stitches.

The invention summarized above comprises the constructions hereinafter described, the scope of the invention being indicated by the subjoined claims.

BRIEF DESCRIPTION OF THE DRAWINGS

In the accompanying drawings, in which several of various possible embodiments of the invention are illustrated, corresponding reference characters refer to corresponding parts throughout the several views of the drawings in which:

FIG. 1A is a side elevation of a surgical needle in accordance with the present invention;

FIG. 1B is a front elevation of the needle shown in FIG. 1A;

FIG. 1C is a side elevation of a surgical needle variant of that shown in FIG. 1A.

FIG. 2A is a side elevation of a second surgical needle in accordance with the present invention;

FIG. 2B is a front elevation of the needle shown in FIG. 2A;

DETAILED DESCRIPTION OF THE INVENTION

Figure 3A:
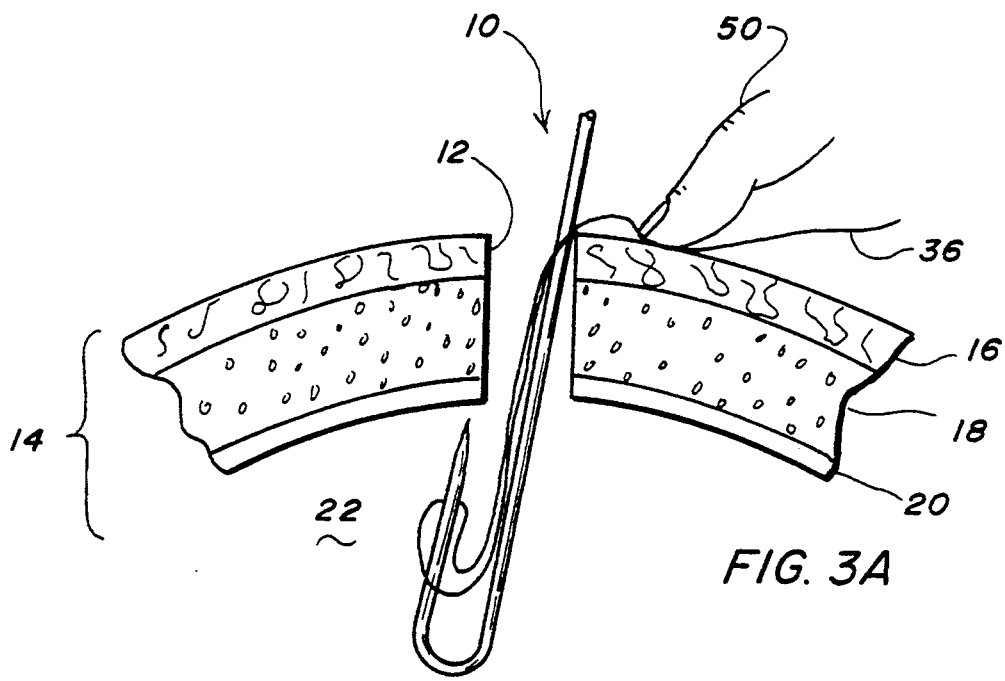
FIGS. 3A-3I are simplified (e.g., interleaved layers of subcutaneous fat and muscle are omitted) diagrammatic successive views in section showing closure of a laparoscopic incision with the surgical needle shown in FIGS. 1A-1B.

Referring to the drawings more particularly by reference characters and starting with FIGS. 1A-1B, reference numeral 10 refers to a surgical needle in accordance with the present invention. Needle 10 is especially designed for use in closing a narrow incision 12 in an abdominal wall 14. As shown in FIGS. 3A-3I, abdominal wall 14 includes layers of skin 16, fascia 18 and peritoneum 20 and incision 12 opens into an abdominal cavity 22.

Needle 10 has an elongated shaft 24 with a proximal end 26 and a distal end 28 U-shaped. Distal end 28 has a proximally directed hook 30. Hook 30 has a first leg attached to the distal end of the shaft and a second leg terminating in a sharpened point 32 with an eye 34 adjacent the point through which a suture 36 is threaded. Suture 36 may be permanent or absorbable and made of nylon or of any other suture material known in the art. Hook 30 is preferably in the same plane as shaft 24 and may be open (e.g., generally "U" shaped with the second leg parallel to the shaft at the point) as shown in FIGS. 1A–1B or partially closed (e.g., generally "C" shaped) with the second leg curved inwardly towards the shaft at the point as shown in FIGS. 2A–2B. For use as described hereinafter, the axis of eye 34 is also preferably in the same plane as shaft 24 (as shown in FIGS. 1A–1B and 3A–3I) but it may be otherwise oriented (as shown in FIGS. 2A–2B and so forth). The body of needle 10 and point 32 may be circular in cross section or of some other shape.

Hook 30 has a width and shape such that it passes through incision 12. Hook 30 has a length such that point 32 can be inserted from the base of the incision through a selected portion of abdominal wall 14 sufficiently far to expose eye 34 from the opening of the incision. The exact width and length of hook 30 will vary with the width and depth of the incision and the tissue type and will also vary with the size of the patient and the amount of fat at the site of the wound.

Needle 10 is especially designed for use in suturing laparoscopic incisions made with a trocar having a diameter larger than 5 mm. The maximum width of hook 30 is preferably about 1 mm smaller than the width of the incision such that when the incision is made with a trocar having a diameter from about 5 mm to about 25 mm, the maximum width of hook 30 is preferably from about 4 mm to about 24 mm, respectively. The length of hook 30 will also vary with the nature of the incision and whether point 32 is inserted through skin 16 and/or peritoneum 20 in addition to fascia 18. In most instances satisfactory results are obtained when hook 30 is from about 1 cm to 10 cm long and the ratio of the length of the leg to the width of the hook is equal to or greater than 2.5. For example, at the lower end of the range, when hook 30 is 4 mm wide and the second leg is 1 cm long, the ratio is 2.5, whereas when the hook is 24 mm wide and the second leg is 10 cm long, the ratio is 4.17. Even higher ratios are possible when hook 30 is less than 24 mm wide.

Shaft 24 preferably is from about 10 cm to 40 cm long. Depth markings 38 may be provided along shaft 24 with a double line at the level of hook 30 and single lines at centimeter intervals.

A means 40 for indicating the location of point 32 is provided on proximal end 26 of shaft 24. As shown in FIGS. 1A–1B and 3A–3I, means 40 comprise a handle 42. Handle 42 is preferably in the same plane as shaft 24 and the axis of eye 34 and may be formed, for example, by bending proximal end 26 of the shaft. As shown in full lines in FIG. 1A, handle 42 may be formed on the same side of shaft 24 as hook 30 (dotted lines) or on the opposite side (full lines).

A bell 44 may be provided on shaft 24 for capping hook 30. As shown in FIGS. 1A–1B and 3G–3H, bell 44 is reciprocated along shaft 24 for this purpose.

A second illustrative surgical needle 10' in accordance with the present invention is shown in FIGS. 2A–2B. In this embodiment, means 40 take the form of indicia 46 on one or more weights 48 attached to proximal end 26 of shaft 24 and the axis of eye 34 is perpendicular to the plane of shaft 24. In this form, the words "right" and "left" serve as suitable indicia 46 on the side edges of weight 48. If eye 34 were in the plane of shaft 24 (a variation on what is shown in FIGS. 2A–2B), then "front" on weight 48 opposite hook 30 would be a suitable indicia.

The needles of the present invention may be made from any material suitable for use in surgical needles, including stainless steel wire, and may have a diameter from about 0.5 mm to about 3 mm depending on the stiffness of the wire. The needles may be manufactured to conform with the above described characteristics by any of the techniques well known in the art of needle manufacturing. One method for manufacturing the needles is to first straighten a length of wire from a coil. The straightened wire may be cut to the desired length. One end of the wire is ground by standard techniques to form point 32. Adjacent point 32, the needle is drilled to provide an eye 34 for attaching suture 36. Eye 34 may be circular, oval, C-shaped and so forth. The wire is then bent to form hook 30 of the desired size and shape at distal end 28 of shaft 24. Direction indicating means 40 are then attached (or formed as by bending) at proximal end 26 of shaft 24.

In use needle 10 (or 10' and so forth) functions as a needle, suture holder and grasper all in one easy-to-use instrument. It uncomplicates closure of laparoscopic incisions and minimizes the risk of incisional hernia formation. It can also be used to ligate an artery (e.g., one accidentally severed on trocar insertion) and, in general, to accurately place a "through and through" suture in a narrow, deep incision.

The following examples illustrate use of the invention.

EXAMPLE 1

A nick or small incision is made in skin 16 of abdominal wall 14 to minimize resistance to entry of a trocar. The trocar punches through skin 16, fascia 18 and peritoneum 20 forming laparoscopic incision 12 through which a cannula is inserted and abdominal cavity 22 is accessed.

After a laparoscopic procedure is completed, the cannula is withdrawn. If the cannula is 10 mm or larger, laparoscopic incision 12 should be closed to prevent possible development of hernias. As shown in FIGS. 3A–3I, this can be accomplished with surgical needle 10.

With reference to FIG. 3A, a length of suture 36 is threaded through eye 34. The ends of suture 36 are dressed together and are held as with a first finger 50 pressing against skin 16 on one side of incision 12 while hook 30 is passed through incision 12.

Figure 3B:
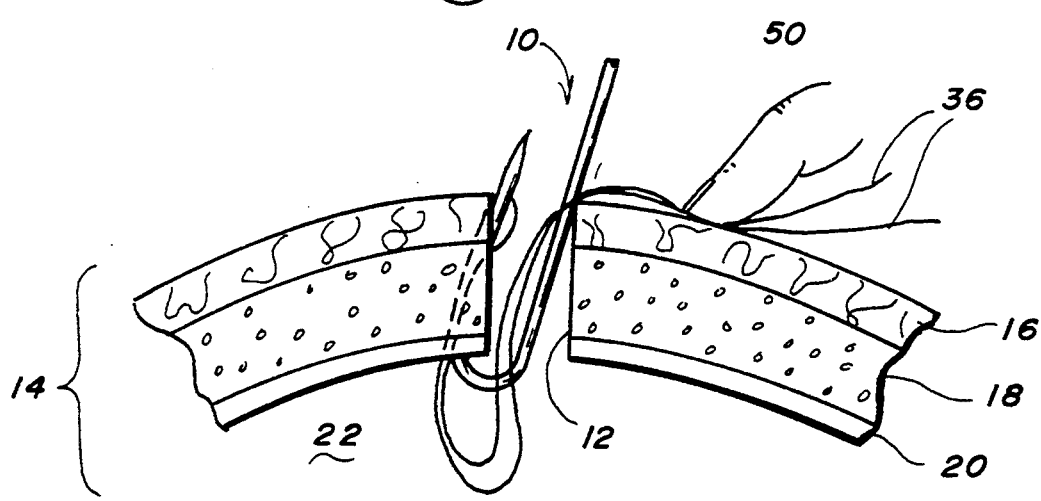
Figure 3C:
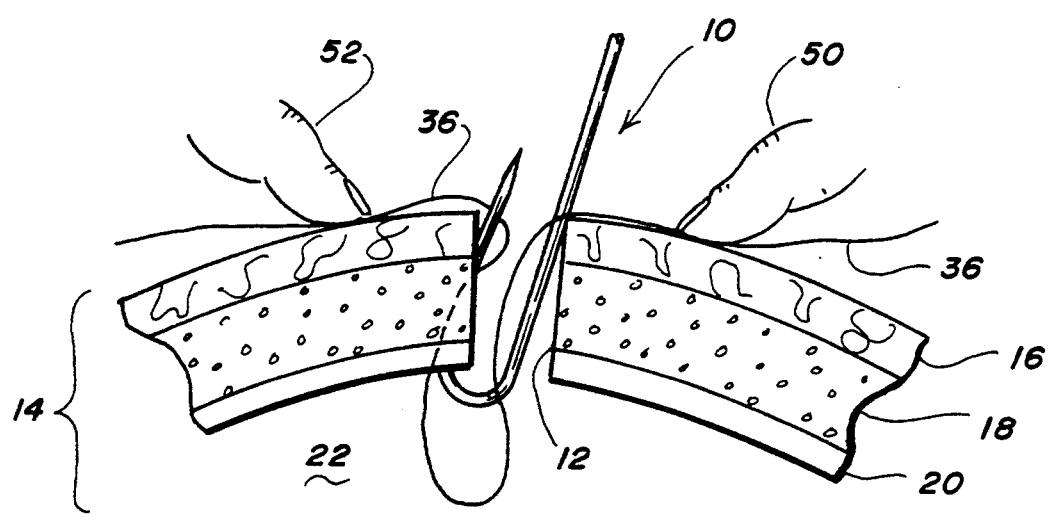

Referring to FIG. 3B, point 32 is inserted through peritoneum 20 and fascia 18 (if it is desired to suture the peritoneum also) and exits just below skin 16. During this operation, handle 42 removes any uncertainty as to the location of point 32 and depth markings 38 may also be of guidance. With reference to FIG. 3C and working from the front or back of eye 34, one of the ends of suture 36 is pulled through the hole made by point 32 and held as with a second finger 52 pressing against skin 16 on an opposite side of incision 12.

Figure 3D:
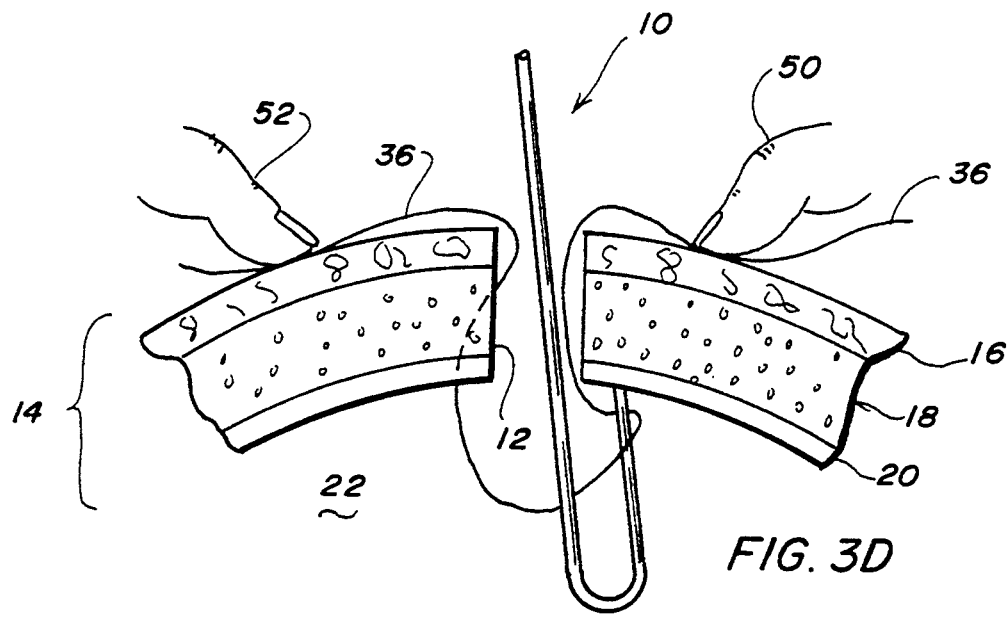
Figure 3E:
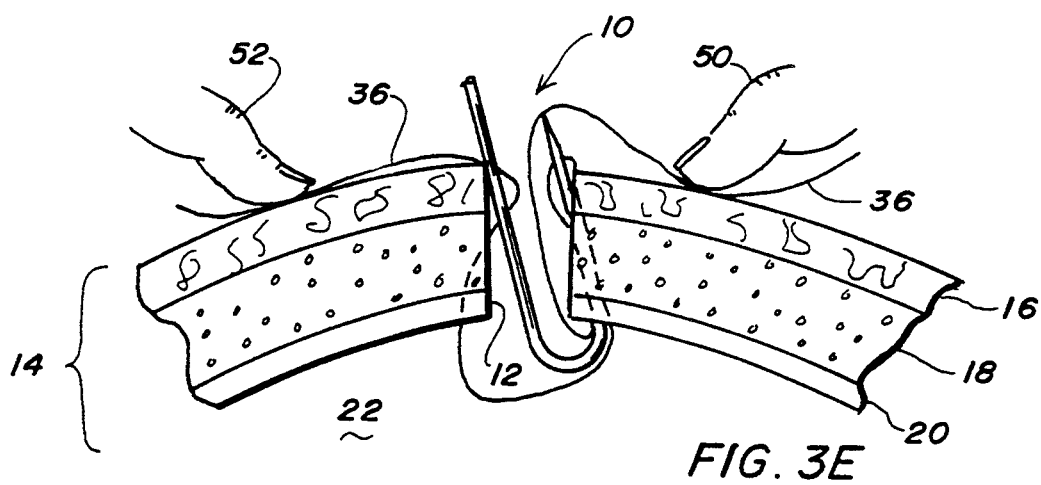

As shown in FIG. 3D, needle 10 is then withdrawn from the hole and inserted into peritoneum 20 and fascia 18 on the opposite side of incision 12. In FIG. 3E, point 32 is shown coming through fascia 18.

Figure 3F:
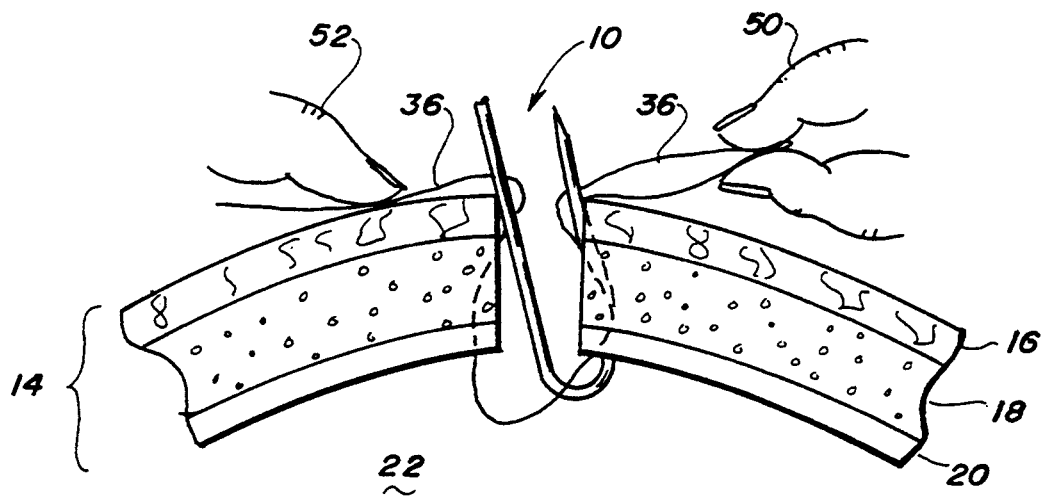

With reference to FIG. 3F, the other end of suture 36 is unthreaded from eye 34 and pulled through the second hole made by point 32. This is accomplished by pulling the suture from the same side of eye 34 as in step 3C (i.e., either from the front or back). If the axis of eye 34 is perpendicular to the plane of hook 30 as in needle 10', the operation of unthreading eye 34 is accomplished by working the suture in steps 3C and 3F from either the right or from the left.

Figure 3G:
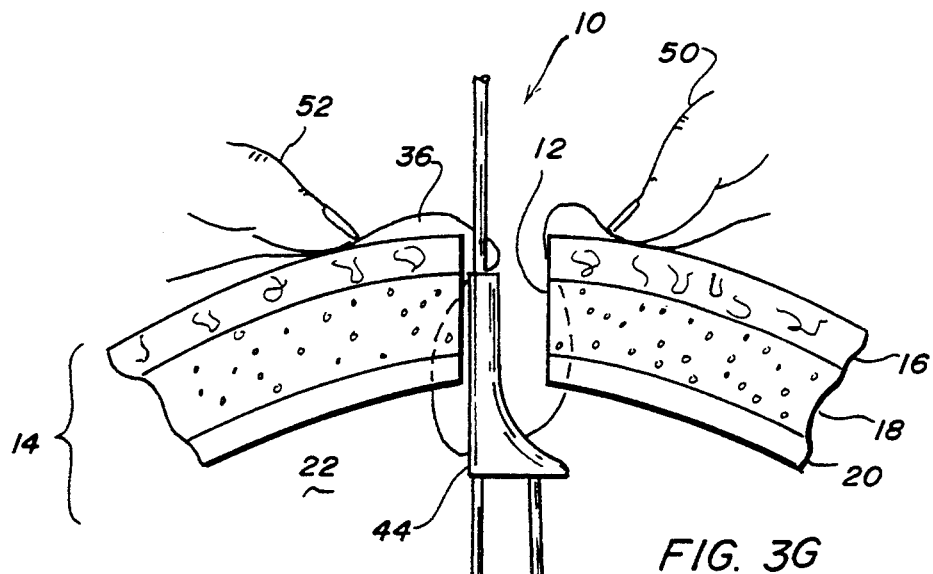

Continuing to FIG. 3G, bell 44 (if present) may be reciprocated down shaft 24 and used to cap hook 30. When point 32 is angled towards shaft 24 as shown in FIGS. 2A-2B and in other instances, step 3G may be eliminated.

Figure 3H:
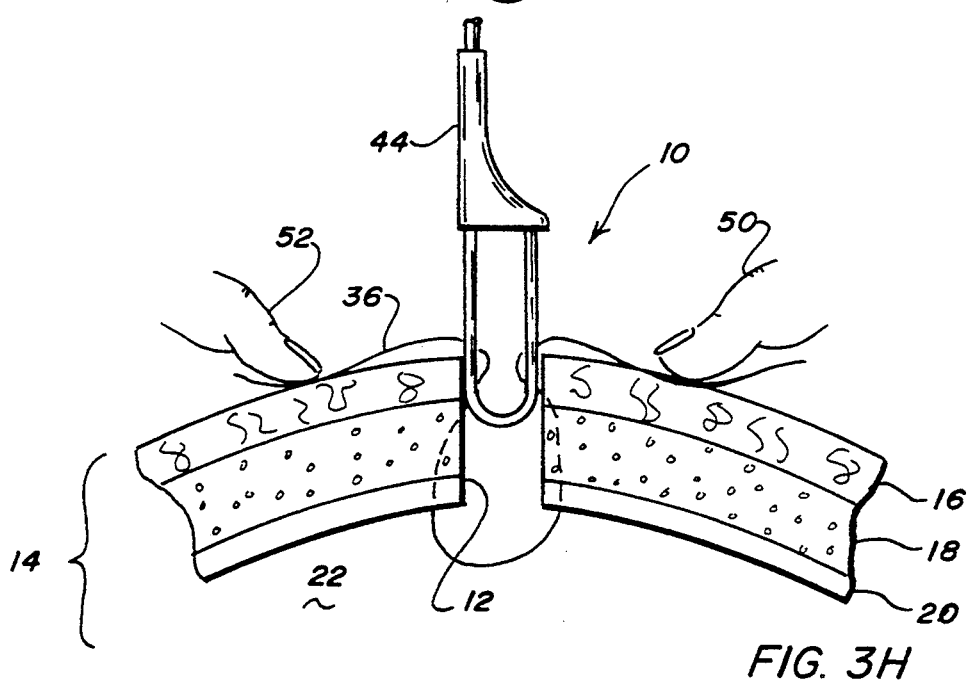

Hook 30 is then pulled out of incision 12 as shown in FIG. 3H. If hook 30 is not capped with bell 44, care must be taken not to hook suture 36 which passes "through and through" on both sides of incision 12.

Figure 3I:
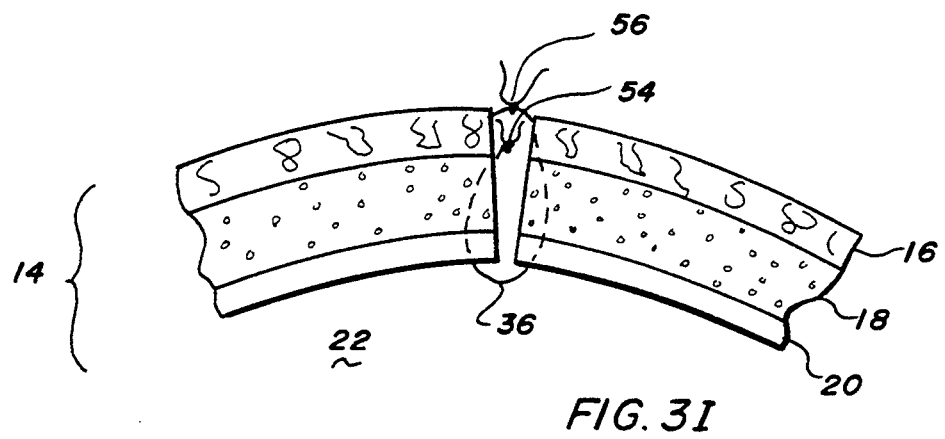

With reference to FIG. 3I, the ends of suture 36 are released from fingers 50, 52 and then tied into a knot 54. As shown, knot 54 is within the incision site and the laparoscopic incision closed. Additional sutures can be placed in the same manner. Skin 16 is then approximated over the deep stitch(es) at 56 to complete the closure.

It will be understood that the ends of the suture may be otherwise immobilized during the steps shown in FIGS. 3A-3H as for example by having an assistant hold the ends.

EXAMPLE 2

Ligating an artery to control hemorrhage

Occasionally, a trocar cuts an artery in abdominal wall 14 (such as an inferior epigastric artery) when laparoscopic incision 12 is made and sometimes it is necessary to ligate the vessel to control hemorrhage. Device 10 is threaded with a suture as described in Example 1 and hook 30 passed through incision 12. Hook 30 can then be used to place a "through and through" suture around the artery working from the base of incision 12. For this purpose, hook 30 must be long enough to pass through skin 16 and expose eye 34. Once the ends of the suture have been brought through the abdominal wall, the ends are tied into a knot with sufficient pressure to ligate the spurting vessel. If there is time, skin 16 may be nicked such that the knot is subcutaneous for cosmetic reasons.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed:

1. A surgical needle having an elongated substantially straight shaft with a proximal end and a distal end, said shaft having a proximally directed U-shaped hook at its distal end, said hook being of a size and shape that the hook passes through a narrow incision in an abdominal wall opening at its base into an abdominal cavity, said hook having a first leg attached to the distal end of the shaft and a second leg terminating in a point with an eye adjacent the point for receipt of a suture, said second leg is parallel to the shaft at the point and having a length such that the ratio of the length of the leg to the width of the hook is equal to or greater than 2.5 in a point with an eye adjacent the point for receipt of a suture whereby the second leg of the hook has a length such that the point can be inserted from the base of the incision through a selected portion of the abdominal wall surrounding the incision sufficiently far to expose the eye from the opening of the incision, and said shaft having a means at its proximal end for indicating the location of the point whereby the needle can be manipulated from the opening of the incision to place the suture through and through the abdominal wall.

2. The needle of claim 1 wherein the hook is in the same plane as the shaft.

3. The needle of claim 2 wherein the axis of the eye is in the same plane as the shaft.

4. The needle of claim 2 wherein a bell is mounted on the shaft for selectively capping the hook.

5. The needle of claim 2 wherein the means for indicating the location of the point is a handle in the same plane as the shaft.

6. The needle of claim 2 wherein the means for indicating the location of the point is a marking on a weight attached to the shaft.

7. A surgical needle having an elongated substantially straight shaft with a proximal end and a distal end, said shaft having a proximally directed U-shaped hook in the plane of the shaft at its distal end, said hook being of a size and shape that the hook passes through a narrow incision in an abdominal wall opening at its base into an abdominal cavity, said hook having a first leg attached to the distal end of the shaft and a second leg terminating in a point with an eye adjacent the point for receipt of a suture, said second leg is parallel to the shaft at the point and having a length such that the ratio of the length of the leg to the width of the hook is equal to or greater than 2.5 whereby the second leg of the hook has a length such that the point can be inserted from the base of the incision through a selected portion of the abdominal wall surrounding the incision sufficiently far to expose the eye from the opening of the incision, and said shaft having a means at its proximal end for indicating the location of the point whereby the needle can be manipulated from the opening of the incision to place the suture through and through the abdominal wall.

8. The needle of claim 7 wherein the hook has a maximum width about 4 mm to 24 mm.

9. The needle of claim 8 wherein the shaft is from about 10 cm to 40 cm long.

10. The needle of claim 9 wherein the hook is from about 1 cm to 10 cm long.

11. A surgical needle having an elongated substantially straight shaft with a proximal end and a distal end, said shaft having a proximally directed U-shaped hook at its distal end, said hook being of a size and shape that the hook passes through a narrow incision in an abdominal wall opening at its base into an abdominal cavity, said hook having a first leg attached to the distal end of the shaft and a second leg terminating in a point with an eye adjacent the point for receipt of a suture, said second leg is curved inwardly towards the shaft at the point and having a length such that the ratio of the length of the leg to the width of the hook is equal to or greater than 2.5 whereby the second leg of the hook has a length such that the point can be inserted from the base of the incision through a selected portion of the abdominal wall surrounding the incision sufficiently far to expose the eye from the opening of the incision, and said shaft having a means at its proximal end for indicating the location of the point whereby the needle can be manipulated from the opening of the incision to place the suture through and through the abdominal wall.

12. The needle of claim 11 wherein the hook is in the same plane as the shaft.

13. The needle of claim 12 wherein the axis of the eye is in the same plane as the shaft.

14. The needle of claim 12 wherein the means for indicating the location of the point is a handle in the same plane as the shaft.

15. The needle of claim 12 wherein the means for indicating the location of the point is a marking on a weight attached to the shaft.

* * * * *